United States Patent [19]
Jacqualt

[11] Patent Number: 5,459,302
[45] Date of Patent: Oct. 17, 1995

[54] APPARATUS AND PROCESS FOR MEASURING THE TEMPERATURE OF A SAMPLE HEATED IN A MICROWAVE CHAMBER

[75] Inventor: Patrick Jacqualt, Sevres, France

[73] Assignee: Societe Prolabo, Paris Cedex, France

[21] Appl. No.: 222,010

[22] Filed: Apr. 4, 1994

Related U.S. Application Data

[63] Continuation of Ser. No. 996,162, Dec. 23, 1992, abandoned.

[30] Foreign Application Priority Data

Dec. 23, 1991 [FR] France .................................. 91 16286

[51] Int. Cl.⁶ .................................................. H05B 6/68
[52] U.S. Cl. .......................... 219/693; 219/700; 219/711; 374/149; 422/21
[58] Field of Search ..................................... 219/700, 701, 219/710, 711, 752, 753, 754, 693; 374/149; 422/21

[56] References Cited

U.S. PATENT DOCUMENTS 2,595,748  5/1952  Andrews .
3,551,090  12/1970 Brumfield et al. .
3,759,102  9/1973  Murray ..................................... 374/123
4,015,476  4/1977  Roche et al. ............................ 374/104
4,163,140  7/1979  Bardet .
4,191,876  3/1980  Ohkubo et al. .
4,444,723  4/1984  Matsumaru et al. .
4,461,941  7/1984  Fukuda et al. .
4,566,809  1/1986  Arnaud .................................... 374/126
4,681,740  7/1987  Commarmot et al. .
4,693,867  9/1987  Commarmot et al. .
4,876,426  10/1989 Smith ....................................... 219/711
4,956,532  9/1990  Koch .
5,059,400  10/1991 Benezech et al. .
5,099,096  3/1992  Kimrey, Jr. et al. .

FOREIGN PATENT DOCUMENTS 2062428  5/1981  United Kingdom .

Primary Examiner—Philip H. Leung
Attorney, Agent, or Firm—Burns, Doane, Swecker & Mathis

[57] ABSTRACT

A sample is heated by microwaves, and the temperature of the sample is measured by a radiation pyrometer arranged to receive radiation directly from the sample. The sample is disposed in a chamber having an orifice dimensioned to block the passage of microwaves, and admit the passage of radiation. The chamber has an upper wall in which one or more openings are formed for receiving a sample-containing receptacle.

9 Claims, 1 Drawing Sheet

APPARATUS AND PROCESS FOR MEASURING THE TEMPERATURE OF A SAMPLE HEATED IN A MICROWAVE CHAMBER

This application is a Continuation of application Ser. No. 07/996,162, filed Dec. 23, 1992, now abandoned.

The present invention relates to measuring the temperature of a sample contained in a receptacle and heated in a microwave chamber. During the application of the microwaves, the temperature of at least one sample is measured.

Such apparatus are described for example in the European patents issued under numbers 0155893, 0156742, and the European Application published under No. 0387161 of the Prolabo Company, which documents correspond, respectively, to U.S. Pat. Nos. 4,681,740, 4,693,867, and 5,059,400.

The sample contained in the receptacle is subjected to microwaves in order to cause its rapid heating, for example, for obtaining a chemical reaction or a physical operation on the sample in a humid environment.

By way of example, one can carry out in such an apparatus chemical reactions such as mineralization, decomposition, and hydrolysis as well as physical operations such as dissolution, crystallization, evaporation, and fusion.

Depending on the chemical reaction and/or physical operation carried out, the receptacle placed in the cavity where microwaves are applied may contain a product or a mixture of products and eventually one or several reagents. For convenience, the contents of the receptacle will be referred to as "Sample".

For measuring the temperature of a sample contained in a receptacle undergoing heating, one generally uses a rod or probe which penetrates to the bosom or core of the sample in the receptacle. Such probes, which are of metal and are connected by conducting wires to a device which gives readings, cannot be used for measuring the temperature of a sample placed in a cavity where microwaves are applied. In effect, such metallic probes and their connecting wires act as antennas and therefore emit microwaves beyond the application cavity, which presents a certain danger.

To avoid the antenna phenomena, it has been proposed to measure the temperature by means of a probe penetrating into the sample, the probe composed of optical fibers which conduct radiation from the sample to an optical pyrometer. This measuring method has advantages, but it is very limited and does not permit following the progress of temperature in a sample on a continuing basis, for example, from ambient temperature to 500° C. or 600° C. In effect, the probe composed of optical fibers only permits the measurement in a well-defined temperature range, which does not permit following continually the rig of temperature in a sample for example, from 20° C. to 500° C., as this requires several changes of the measuring probe.

Also, when chemical reactions in a humid environment are carried out, such as mineralizations, the reaction medium is very corrosive, which adversely affects the reliability of the measurement and the life of the optical fibers.

An object of the invention is to provide a temperature measuring apparatus and process for samples placed in an apparatus using microwaves, which permits continuous measurement of the sample temperature and permits one to follow its evolution.

Another object is to provide such an apparatus and process which prevents any escape of microwaves outside the cavity where they are applied.

Finally, still another object of the invention is to provide an apparatus and process which applies microwaves to at least one sample, comprising temperature measurement means without polluting the ambient environment of the apparatus by microwaves, and such that the temperature can be measured continuously.

SUMMARY OF THE INVENTION

A temperature measurement apparatus has now been discovered for measuring the temperature of a sample placed in a microwave device by measuring radiation from the sample directly by means of a irradiation pyrometer.

By "radiation pyrometer" is meant an instrument which measures temperature as a function of radiation and includes a pyrometer which collects both visible and invisible radiation as well as a pyrometer which collects solely visible radiation.

In the present text, "directly" means that the radiation emitted by the sample reaches the irradiation pyrometer without being conducted through any glass intermediary, such as a bundle of optical fibers. Stated in another way, the radiation travels freely in the atmosphere from the sample to the irradiation pyrometer, with or without the use of a minor for reflecting the radiation.

An apparatus for carrying out the process comprises means for emitting microwaves to an application cavity or chamber, circumscribed by a wall, the sample-containing receptacle being placed in said chamber. The chamber includes an orifice which is permeable to radiation and impermeable to microwaves. Radiation passes through the orifice and is directed to the temperature sensor.

According to another embodiment, microwaves are applied simultaneously to a plurality of samples, each sample being placed in a receptacle. The receptacles are disposed in the application chamber along a circle having an axis X. The receptacles can be rotated around the axis X.

The means of temperature measurement is constituted by a radiation pyrometer receiving directly the irradiation emitted by the sample through an orifice in the wall of the chamber where microwaves are applied.

In order that the orifice in the wall of the application chamber does not constitute a source of pollution of the environment with microwaves, the dimensions of the orifice are such that it forms a barrier against the propagation of microwaves outside the chamber.

According to another embodiment, in order equally to prevent the escape of microwaves through the orifice, there is associated with the orifice a chimney having a height which is a function of the emission frequency of the microwaves and of the orifice cross-section in order to form a barrier for absorption of the microwaves.

According to a different embodiment, a mirror is placed in such a manner that it reflects the radiation toward the radiation pyrometer.

The apparatus of the present invention is designed to submit the sample, contained in the receptacle, to microwaves in order to heat them rapidly, such heating having as its aim the carrying out of a physical or chemical operation on the sample.

The apparatus is thus particularly intended for subjecting the samples to chemical reactions in a humid environment.

The present invention also relates to a process for heating a sample and measuring the temperature thereof.

BRIEF DESCRIPTION OF THE DRAWINGS

The invention will be better understood from the description of the accompanying figures which represent, by way of example, schematically, without any definite scale, various embodiments of the apparatus of the invention for carrying out a process according to the invention.

DETAILED DESCRIPTION OF PREFERRED EMBODIMENTS OF THE INVENTION

Figure 1:
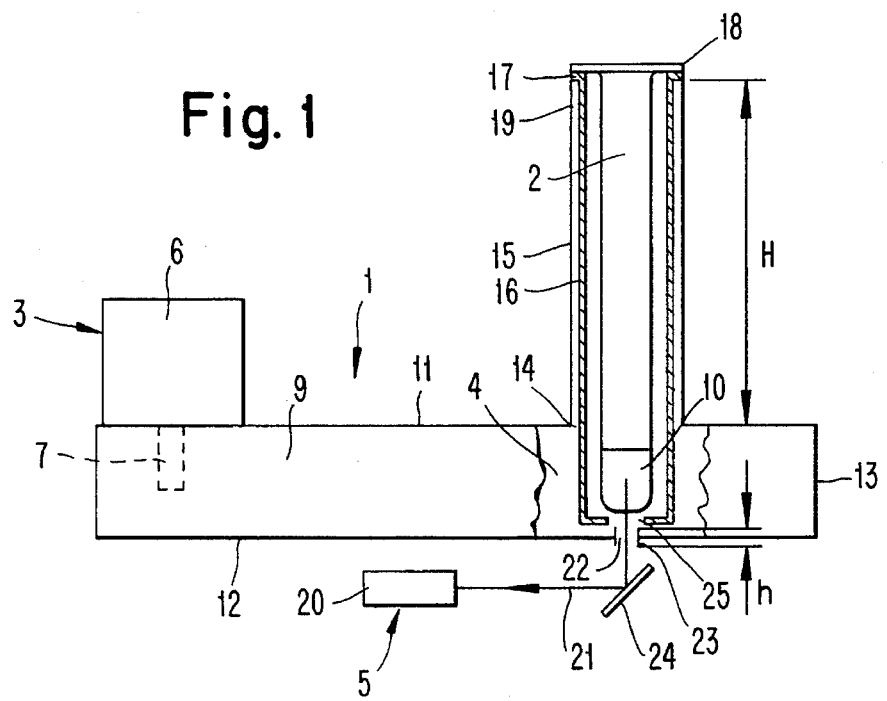
FIG. 1 is a schematic side view, partially in section, of a first embodiment of an apparatus according to the invention.

An apparatus (1) for applying microwaves to a sample (10) placed in a receptacle (2), according to the invention, represented in FIG. 1, comprises a means (3) for emitting microwaves in an application cavity or chamber (4) in which is placed the receptacle (2), and a means (5) for measuring the temperature of the sample (10).

The means (3) for emitting microwaves is constituted by a microwave generator (6) comprising an antenna (7) emitting microwaves in a wave guide (9) that is connected with the application chamber (4).

The wave guide (9) is of substantially parallelepipedic or right rectangular cross-section, the application chamber (4) being formed by a zone of the wave guide (9) located opposite the antenna (7). The application chamber (4) is thus formed by an upper wall (11) lower wall (12) and side wall (13) of the wave guide (9).

In order to introduce receptacle (2) into the application chamber (4), the upper wall (11) contains a suitably dimensioned opening (14). If receptacle (2) is of circular cross-section, opening (14) is likewise circular. According to the illustrated embodiment, receptacle (2) is a test tube and comprises a flange (18) projecting outwardly from its upper end.

Opening (14) is provided with an upstanding chimney (15). The chimney has a height H, which is a function of the emission frequency of the microwaves and of the cross-section of the opening (14) in order to form an absorption barrier against the propagation of microwaves outside the application chamber (4). The chimney (15) is preferably a cylindrical tube formed of sheet metal.

Between chimney (15) and the receptacle (2) is placed a sheath (16) made of material permeable to microwaves. If the receptacle (2) were to break, the sheath (16) would prevent the entry of sample (10) and fragments of receptacle (2) into the chamber (4). The sheath (16) comprises at its upper portion a flange (17).

Flange (17) of sheath (16) rests on the upper surface (19) of chimney (15), and flange (18) of receptacle (2) rests on flange (17).

The means (5) for measuring the temperature of sample (10) are constituted according to the invention by an irradiation pyrometer (20) receiving directly the radiation (21) emitted by the sample (10). By "directly" is meant that the radiation (21) is not conducted by an intermediary, such as a bundle of optical fibers, to the radiation pyrometer, but rather travels freely in the atmosphere.

The radiation pyrometer (20) receives the radiation (21) through an orifice (22) formed in the lower wall (21) of the application chamber (4).

According to the illustrated embodiment, there is associated with orifice (22) a chimney (23) of a height h which is a function of the emission frequency of the microwaves and of the cross-section of the orifice (22) in order to form, similar to the opening (14), an absorption barrier for microwaves.

Likewise according to the illustrated embodiment, the radiation (21) emitted by sample (10) through orifice (22) is reflected by a mirror 24 toward the radiation pyrometer (20). The sheath (16), which is not permeable to radiation (21) emitted by sample (10), is provided with a hole (25) aligned with orifice (22).

Thus, when the apparatus is in operation, the temperature of sample (10) contained in receptacle (2) is measured by a radiation pyrometer (20), which directly receives radiation (21) emitted by sample (10) via the hole (25) of sheath (16), the orifice (22) of the application chamber (4) and the mirror (24).

The temperature of sample (10) can be measured continuously or discontinuously; it can be displayed and read directly by the operator and/or recorded by a printer; the irradiation pyrometer (20) can be connected to printing means or to photographic recording means.

Figure 2:
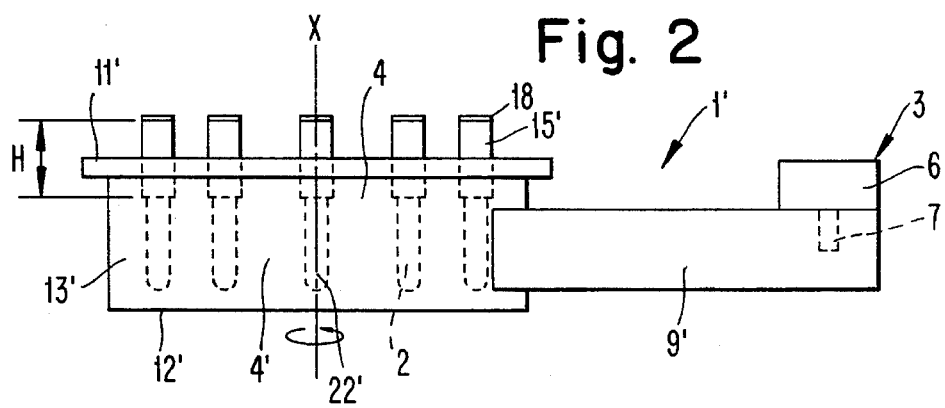
FIG. 2 is a schematic side view of another embodiment of an apparatus according to the invention.

Another embodiment according to the invention, illustrated in FIG. 2, permits the application of microwaves simultaneously to a plurality of samples, each sample being placed in a respective receptacle (2). The application chamber (4'), which comprises an upper wall (11'), a lower wall (12'), and a lateral wall (13') is in the form of a cylinder having an axis X extending perpendicular to the direction of displacement of the microwaves in the microwave guide (9'). The upper wall (11') is movable independently of the side wall (13') and may be rotated relative thereto about a central axis X. The upper wall (11') is thus provided at its periphery with means which cooperates with means carried at the upper edge of the lateral wall (13') to form a trap for microwaves, and to facilitate the relative displacement of the upper wall (11') relative to the side wall (13') by reducing frictional force.

The apparatus (1') allows one to introduce into the application chamber (4') eight receptacles (2), each containing a sample. These receptacles (2) are introduced in to the application chamber (4') through openings in the upper wall (11') which are provided as described above with chimneys (15') of height H. Lower portions of the chimneys (15') are situated in the chamber (4').

The openings in the upper wall (11') of the application chamber (4') are arranged in a circular array about axis X. The receptacles (2) and hence, the samples which they contain, are thus all submitted to the same quantity of microwaves upon rotation of the upper wall (11') around axis X.

In FIG. 2, a single orifice (22') is provided in side wall (13') and is arranged so that the receptacles sequentially pass thereacross. A discontinuous temperature measurement of a sample is thereby performed, the temperature in effect being measured each time the sample passes across orifice (22').

Alternatively, in order to carry out temperature measurements at more frequent time intervals, the side wall (13') may comprise several orifices (22'), each orifice (22') having associated with it a radiation pyrometer (not shown in FIG. 2).

Alternatively, the receptacles and all of the walls of the application chamber could be fixed against rotation, and the side wall provided with a plurality of orifices associated with respective receptacles. Each orifice would be associated with its own radiation pyrometer, or else the operator could displace a single radiation pyrometer across all of the openings in sequence in order to associate it successively with each orifice.

Figure 3:
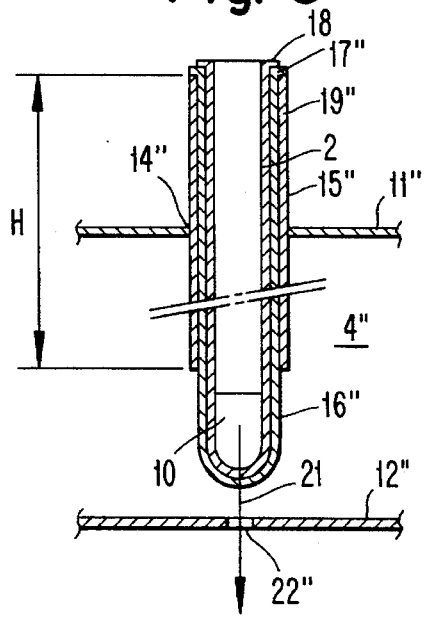
FIGS. 3 and 4 are fragmentary views, in vertical section, of two other embodiments according to the invention.

FIG. 3 is a detailed view in section along a vertical plane of another embodiment according to the invention wherein the chamber (4") is circumscribed by an upper wall (11"), a lower wall (12"), and a side wall (not shown). The upper wall (11") has at least one opening (14") for the introduction into the application chamber (4") of a receptacle (2). Opening (14") is provided, as before, with a chimney (15") of a height H forming an absorption barrier for microwaves. The chimney (15") is, according to the present embodiment, partially situated in the chamber (4").

In chimney (15") is a placed sheath (16") made of material which is permeable to microwaves and to radiation (21) emitted by the sample (10).

As before, the sheath (16") rests on the upper surface (19") of chimney (15") via flange (17"), and the receptacle (2) rests on the sheath via flange (18).

The means for measuring the temperature of sample (10) are constituted by radiation pyrometer (not shown) receiving the radiation (21) emitted by sample (10) through an orifice (22") situated in the lower wall (12") of chamber (4"). Orifice (22") is not like orifice (22) of apparatus 1 illustrated in FIG. 1 which is surrounded by a chimney of height h. No such chimney is provided in FIG. 3. Rather, the dimensions of orifice (22") have been calculated here such that the orifice itself constitutes a barrier against the propagation of microwaves.

Figure 4:
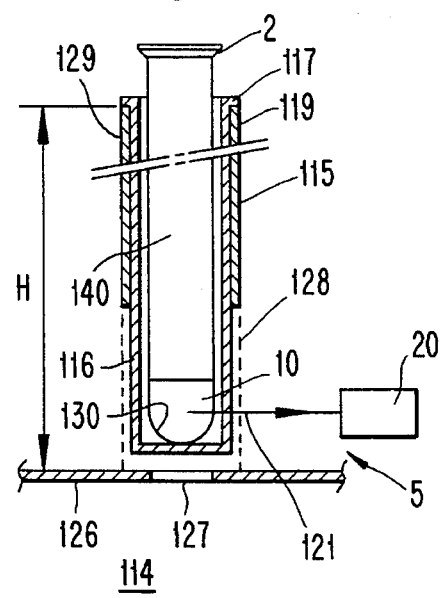

A further embodiment is depicted in FIG. 4 in which chimney (115) is shown in vertical section. Microwaves are emitted in a cavity (114) having an upper wall (126) provided with at least one connecting window (127). Each connecting window (127) is surrounded by a cylindrical chimney (115) located above the upper wall (126).

The interior space of chimney (115) forms an application chamber (140) intended to receive the receptacle 2.

Chimney (115) according to this embodiment has a lower end (128) formed by a discontinuous or non-solid structural material, such as a metal cloth, and an upper part (129) formed by a solid or continuous structural material, such as sheet metal. The chimney has a height H which is a function of the emission frequency of the microwaves in the cavity (114) and of the cross-section of the connecting window (127) in order to prevent the propagation of microwaves from the application chamber (140).

In chimney (115) there is placed a sheath (116) which rests via flange (117) on the upper edge (119) of chimney (115). According to this embodiment, the lower part (130) of the receptacle (2) rests on the bottom of sheath (116) directly or after insertion of a shock absorbing material therebetween.

Sheath (116) is made of material which is permeable to microwaves and to radiation (21) emitted by sample (10). The radiation from the sample is received by means (5) for measuring the temperature of sample (10). That is, the radiation pyrometer (20) receives directly the radiation (21) emitted by sample (10) through the gaps in the discontinuous construction material which constitutes the lower part (128) of chimney (115).

The invention is not limited to the embodiments illustrated and described above, and one can, within the scope of the present invention, combine among them the various described features. Equally part of the present invention, are other variations or embodiments within the skill of persons skilled in the art.

Thus, the chamber for the application of microwaves, which has been described above as being of circular cross section, can likewise be in the form of a cylinder which is of non-circular cross section, for example, polygonal.

The receptacles containing the sample have been described above as being test tubes, but they can of course be replaced by other receptacles of a material permeable to microwaves, such as hard glass tubes, bulbs, etc.

Likewise, while the receptacles have been described as open at their tops, they can be provided in the upper part with means for capturing fumes and vapors emitted by the sample upon the application of microwaves or they also can be provided with stoppers assuring a tight closure of the receptacle in such a fashion that it is capable of supporting internal pressure.

The apparatus of applying microwaves to at least one sample and the process for measuring the temperature of a sample according to the invention, present numerous advantages. In particular, the measurement of the temperature of the sample can be carried out continuously or discontinuously in the application chamber, without the risk of microwaves escaping to the outside. In addition, the measurement of temperature of very highly corrosive samples can be carried out because the process does not require the use of probes extending into the sample.

The apparatus for application of microwaves to at least one sample and the process for measuring the temperature of the sample are particularly suitable for use for chemical reactions in a humid medium.

What is claimed is:

1. Apparatus for heating a sample and measuring the temperature thereof, comprising:

a chamber, means for introducing microwaves into the chamber, receptacle-receiving means including at least one chimney extending upwardly from the chamber and having an open upper end, the at least one chimney being dimensioned to block the passage of microwaves from the open end, a receptacle seated in the at least one chimney such that a lower end thereof which contains a sample is disposed within the chamber and is heated by the microwaves so as to emit radiation, the chamber including an orifice formed under the receptacle in a lower wall of the chamber an dimensioned to block the passage of microwaves and permit the passage of the radiation, and a pyrometer arranged for directly receiving the radiation emitted by the sample through the orifice and reflected by a mirror.

2. Apparatus according to claim 1, wherein the at least one receptacle-receiving means comprises a plurality of receptacle-receiving means each receiving a receptacle, and further including displacing means for displacing the receptacle-receiving means and said chimneys together in the chamber.

3. Apparatus according to claim 2, wherein the displacing means comprises means for rotating about a vertical axis a member which carries the plurality of receptacle receiving means.

4. Apparatus according to claim 1, wherein the at least one receptacle-receiving means includes a sheath disposed in the chimney and surrounding at least the lower portion of the receptacle, the sheath being permeable to microwaves.

5. Apparatus according to claim 4, wherein the sheath includes an opening aligned with the orifice for passing radiation.

6. Apparatus according to claim 1, wherein the at least one receptacle-receiving means includes a support surface upon which the receptacle is supported.

7. Apparatus according to claim 6, wherein the support surface supports an upper end of the receptacle.

8. Apparatus according to claim 6, wherein the support surface supports a lower end of the receptacle.

9. A process for heating a sample and measuring the temperature thereof, comprising the steps of:

seating a receptacle within a chimney which extends upwardly from a microwave chamber and which is dimensioned to block the passage of microwaves from the chamber, introducing microwaves into the chamber to heat a sample contained in a lower portion of the receptacle, the heated sample emitting radiation which travels freely within the atmosphere and passes through an orifice located under the receptacle in a lower wall of the chamber, causing the radiation from the orifice to travel to a pyrometer, and removing the receptacle upwardly from the receptacle-receiving means.

* * * * *

UNITED STATES PATENT AND TRADEMARK OFFICE
CERTIFICATE OF CORRECTION

PATENT NO. : 5,459,302
DATED : October 17, 1995
INVENTOR(S) : Patrick JACQUAULT It is certified that error appears in the above-identified patent and that said Letters Patent is hereby corrected as shown below:

ON THE TITLE PAGE:

[75] Inventor: Patrick Jacqualt

Change to -- Patrick JACQUAULT --

Signed and Sealed this

Third Day of September, 1996

Attest:

BRUCE LEHMAN

Attesting Officer     Commissioner of Patents and Trademarks